United States Patent
Richer

(10) Patent No.: US 11,090,274 B2
(45) Date of Patent: Aug. 17, 2021

(54) FORMULATION AND METHOD FOR SUPPORTING RETINAL HEALTH THEREBY REDUCING THE RISK OF AGE-RELATED MACULAR DEGENERATION (AMD)

(71) Applicant: Stuart Richer Consulting, LLC, Highland Park, IL (US)

(72) Inventor: Stuart Richer, Highland Park, IL (US)

(73) Assignee: Stuart Richer Consulting, LLC, Highland Park, IL (US)

(*) Notice: Subject to any disclaimer, the term of this patent is extended or adjusted under 35 U.S.C. 154(b) by 0 days.

(21) Appl. No.: 16/810,413

(22) Filed: Mar. 5, 2020

(65) Prior Publication Data

US 2020/0289427 A1    Sep. 17, 2020

Related U.S. Application Data

(60) Provisional application No. 62/817,949, filed on Mar. 13, 2019.

(51) Int. Cl.
| | |
|---|---|
| *A61K 31/047* | (2006.01) |
| *A61K 31/355* | (2006.01) |
| *A61K 31/375* | (2006.01) |
| *A61K 31/09* | (2006.01) |
| *A61K 33/30* | (2006.01) |
| *A61K 45/06* | (2006.01) |
| *A61K 31/05* | (2006.01) |
| *A61K 33/34* | (2006.01) |

(52) U.S. Cl.
CPC .......... *A61K 31/047* (2013.01); *A61K 31/05* (2013.01); *A61K 31/09* (2013.01); *A61K 31/355* (2013.01); *A61K 31/375* (2013.01); *A61K 33/30* (2013.01); *A61K 33/34* (2013.01); *A61K 45/06* (2013.01)

(58) Field of Classification Search
CPC ........ A61K 31/05; A61K 33/34; A61K 31/07; A61K 31/375; A61K 33/30; A61K 31/355; A61K 31/047; A61K 31/09; A61K 45/06; A61K 2300/00
See application file for complete search history.

(56) References Cited

U.S. PATENT DOCUMENTS

| | | | | |
|---|---|---|---|---|
| 2011/0262553 | A1* | 10/2011 | Jensen | A23L 33/15 424/548 |
| 2012/0258168 | A1* | 10/2012 | Montesinos | A61K 31/202 424/455 |
| 2018/0042894 | A1* | 2/2018 | Olmiere | A61K 33/34 |

FOREIGN PATENT DOCUMENTS

| | | | | |
|---|---|---|---|---|
| EP | 3106158 A1 | * | 12/2016 | ............ A61K 33/06 |
| WO | WO-2006055526 A2 | * | 5/2006 | ............ A61K 33/34 |

* cited by examiner

*Primary Examiner* — Blessing M Fubara
(74) *Attorney, Agent, or Firm* — Dykema Gossett PLLC

(57) ABSTRACT

A formulation and method for comprehensively supporting retinal health and thereby preventing, reducing the risk of, and/or slowing the progression of Age-Related Macular Degeneration (AMD) are disclosed. The formulation includes optimal daily dosages of vitamin C, vitamin E, zinc, copper, lutein, and zeaxanthin.

7 Claims, 3 Drawing Sheets

Figure 1

Components of the Enhanced AREDS II Formulation

| | Preferred Form | 1 gel cap | Daily Minimum Dose | Maximum Dose | Primary Design Consideration(s) | Secondary Design Consideration(s) | Other Considerations i.e. public health |
|---|---|---|---|---|---|---|---|
| AREDS II LEGACY | | | | | | | |
| Vitamin C | Ascorbic Acid | 125- 250 mg | 250-500 mg | 2000 mg | Same, maintain acidity for absorption - enhanced w polyphenol blend and other antioxidants | | |
| Vitamin E | Alpha-tocopherol succinate | 15 IU | 30 IU | 100 U | Save $ and space w/o loss of AREDS 2 / 3 effectiveness | Tocotrienols too expensive and bulky, synergy with selenium | Succinate form found to inhibit cancer |
| Zinc | Zn Carnosine (or monomethionine, citrate, or acetate form) | 12.5 -15 mg | 25 mg | 30 mg | Ongoing NEI - "perceived" scientific issue w high dose zinc and CFH potentiation | Will achieve 70 % higher absorption w B6 in this enhanced formulation | Benefit against H Pylori pathogen (found in 50% of world) |
| Copper* | Cu sulfate chelate | 250 mcg | 250 mcg | 500 mcg | "Avoid high dose AREDS 2 copper oxide that exacerbates AMD | Stable form | copper niacin (cunermuspir or MitoSynnergy® too expensive |
| Lutein | non- esterified | 4.5 mg | 9 mg | 12 mg | Effective Legacy component for low intake consumers | | 3:1 L / Z Ratio in blood per Fred Kasich, PhD |
| Zeaxanthin | natural (3R-3'R) | 1.5 mg | 3 mg | 4 mg | Effective legacy component but higher dose for foveal protection | Long term effect of (3R, 3'S) meso-zeaxanthin unknown | 3:1 L / Z Ratio in blood per Fred Kasich, PhD |
| AREDS II ENHANCERS | | | | | | | |
| Astaxanthin | Astaxanthin (e.g. AstaReal ®) | 1.5 mg | 3 mg | 12 mg | Mitochondria, anti-oxidant, anti-inflammatory, anti-neovascular | Supported by 60 publications, desirable for Chromosome 10 defect carriers | 15 mg total carotenoids to support higher BMI AMD patients |
| Chromium | Chromanex 3+® or other | 50 mcg | 50 mcg | 100 mcg | Concurrent common insulin resistance in AMD patients | Concurrent diabetes and prediabetes | |
| Selenium | selenomethionine or SelenoExcell® | 25 mcg | 50 mcg | 100 mcg | Vit E synergy, GSH - p cofactor releases ZN from binding metallothionine | | |
| 5 B Vitamin complex | | | | | | | |
| B1 (thiamin) | benfotiamine or allithiamine | 2.5 mg | 5 mg | 10 mg | Benefits AMD patients w Dx of NAFLD / diabetes comorbidity & coffee/ soda/ fruit juice consumers | Low dose; allithiamine crosses blood-retinal barrier | Reduces amyloid beta in brain (AD) / drusen |
| B3 (niacin) | niacinamide, niacinamide ascorbate | 25 mg | 50 mg | 250mg | Mitochondrial support, synergy w polyphenols, HZ Chromosome 10 defect | senolytic synergy w pterostilbene and resveratrol | Benefits AMD patients w homozygous chromosome 10 defect |
| B6 (pyridoxine) | 5P 5 (pyridoxal 5'-phosphate) | 25 mg | 25 mg | 50 mg | Benefit AMD patients against US high protein diet and enhances ZN absorption | Also Knocks down High HCY found in many AMD patients | (18% of US population genetically under-methylate) |
| B9 (natural folate) | L 5 folate methyltetrahydrofolate CA salt | 100 mcg | 100 mcg | 200 mcg | Secondary knock down of high HCY in undermethylating AMD patients | Multivitamins typically have synthetic folic acid - problematic | |
| B12 (methylcobalamin) | methyl / hydroxocobalamin | 150 mcg | 150 mcg | 300 mcg | Primary nutrient to knock down high HCY in undermethylating AMD patients; neural architecture in GA AMD | 40 % of US public sub optimal w their multivitamin, higher dose important | Protection of ocular / cerebral tissue in those on chronic GI acid blockade |
| Decalcification Complex | | | | | | | |
| Vitamin D3 | D3 (1400 IU) | 2000 IU | 2000 IU | 8000 IU | Protects Bruch's membrane / Capillaries at every stage of AMD; improves endothelium function, senolytic | 40-70 % of US public sub optimal (would achieve approx. 2000 IU w this formula) Support visual pathway, knock down inflammation | 40-70 % of US public sub optimal (only approx. 400-600 IU in most multis) |
| Vitamin K2 | MK7 and bulky nutrient | 25 mcg | 25 mcg | 120 mcg | Protects Bruch's membrane / Capillaries at every stage of AMD | | US public deficient from poor microbiome |
| Antiangiogenic / anti-VEGF | | | | | | | |
| Polyphenol Blend | cost effective alternative | 125 mg | 250 mg | 1000 mg | Grape seed proanthrocyanidin, quercetin, cinnamaldehyde extract, Cinnulin PF® water sol | | |
| Bioquercetin phytosome | 98% purity | 25 mg | 10 mg | 30 mg | Inexpensive iron chelator to foment angiogenesis | senolytic | protects against NAFLD and viruses |
| Other i.e. Resveratrol or pterostilbene | 80% polygonum cuspidate (low Inodium for resveratrol | 15 mg | 30 mg | 100 mg | Inexpensive copper chelator to foment angiogenesis | Multiple actions including microRNA modulation (see Mechanism Grid), senolytic w vitamin B3 | An anti-aging nutrient |
| CONSUME WITH (optional) | | | | | | | |
| DHA 1 EPA liquid blend | lemon flavored, high DHA | 3-5 tbsps. | varies | | Dose based on RBC omega III index – blood test | The anti-angiogenic component of fish oil | |

Figure 2
Biochemical Mechanisms of Action

| | Bruch's Mb retinal Anti-calcification | Binding Labile FE++ / CU++ Oxidation reduction | Lipofuscin Reduction | Drusen Reduction | Antioxidant or (AO enzymes) | GENETIC Anti-inflammatory (CFH 1 HZ mutation) | GENETIC Mitochondrial Health (ARMS2 / HTRA1 HZ mutation) | Methylatation Support MFTHR and others | Micro- Capillary Health and/or Blood Flow | CONCURRENT IR / DIABETIC RETINOPATHY | Senolytic |
|---|---|---|---|---|---|---|---|---|---|---|---|
| AREDS II LEGACY | | | | | | | | | | | |
| Vitamin C | x | x | x | x | x | x | x | x | x | x | x |
| Vitamin E | | x | x | x | x | | x | | x | x | |
| Zinc | | x | x | x | x | x | x | | | x | |
| Copper* | | | | | x | | | | | | |
| Lutein | | | x | x | x | x | | | x | x | |
| Zeaxanthin | | | x | x | x | x | | | x | x | |
| AREDS II ENHANCERS | | | | | | | | | | | |
| Astaxanthin | x | | | | x | x | x | | x | x | x |
| Chromium | | | | | | | | | x | x | |
| Selenomethionine (ZN release) | | | x | | x | | | | x | x | |
| 5 B Vitamin complex | | | | | | | | | | | |
| B1 (thiamin) | | | | | | | | | | | |
| B3 (niacin) | | | | x (animals) | | x (animals) | x | | x | | x |
| B6 (pyridoxine) (ZN absorption) | | | x | x | | | | x | x | | |
| B9 (folate) | | | | x | | | | x | x | | |
| B12 (cobalamin) | | | | | | | | x | x | | |
| Bruchs Mb | | | | | | | | | | | |
| Vitamin D3 | x | | | | x | x | x | | x | x | x |
| Vitamin K2 MK7 | x | | | | x | x | | | x | x | |
| Anti-VEGF Anti-Inflam Polyphenol mix | x | x | x | | x | x | x | x | x | x | x |
| Bioquercetin phytosome | | x (iron) | | | x | x | | | x | x | x |
| Other -i.e. resveratrol, luteolin, rutin | | x (copper) | x | | x | x | x | x | x | x | x |
| CONSUME WITH (optional) | | | | | | | | | | | |
| DHA essential oil (separate gel cap) | | | x | x | | x | x | | x | x | x |

GLOSSARY
AO = antioxidant
CFH = Complement Factor H
AMD gene ARMS2 / HRTA1 = AMD gene at 10q26
MFTHR = methylene tetrahydrofolate reductase
IR = Insulin Resistance
Senolytic- nutrients that induce death of senescent cells

Figure 3
General Description

| | MARKETING CLAIM(S) | CLAIM 2 | CLAIM 3 |
|---|---|---|---|
| AREDS II LEGACY | "Builds upon 'gold standard' AREDS I and II Science supported by NEI and B+L" | Enhanced AREDS I1- Contains the same active AREDS II legacy ingredients | Certified vegan, gluten-free, non-GMO, & NSF Certified |
| Vitamin C | Still in enhanced AREDS II | Bio-enhanced with polyphenols | |
| Vitamin E | Still in enhanced AREDS II | | |
| Zinc | "Still in enhanced AREDS II but reduced dose for those genetically susceptible to AMD" | Bio-enhanced for 2 vulnerable genetic subgroups | |
| Copper* | Still in enhanced AREDS II | | |
| Lutein | Still in enhanced AREDS II | | |
| Zeaxanthin | "Still in AREDS II, more protection for your fovea" | | |
| AREDS II ENHANCERS | | | |
| Astazanthin | "Supports healthy retinal energy, capillary blood flow and retinal cell membranes" | Defends your mitochondria | Decreases ocular fatigue |
| Chromium | "Supports healthy retinal sugar metabolism" | | |
| Selenium | "Enhanced protection of retinal antioxidant enzymatic systems" | Works synergistically with vitamin E | |
| 5 B Vitamin complex | "Supports healthy retinal metabolism beyond your daily multivitamin" | | |
| B1 (thiamin) | "Protects against excessive coffee, tea and sugared fruit juice /soft drink intake" | | |
| B3 (niacin) | "Protects the mitochondria," clears senescent cellular waste | | |
| B6 (pyridoxine) | "Protects against excess dietary protein" | | |
| B9 (folate) | "Protects approx. 18 % of Americans who undermethylate" | | |
| B12 (cobalamin) | "Protects neural retinal tissue | | |
| Decalcification Complex | "Decalcifies important retinal tissues and their fine ocular capillaries " | | |
| Vitamin D3 | "Important AMD protective nutrient" | Repletes 70% of the US population | |
| Vitamin K2 | "Supports proper retinal calcium distribution" | | |
| Polyphenols | "Like Carotenoids, Found in Fruits and Vegetables, but missing in AREDS II" | Potent anti-inflammatory and healthy aging of retinal tissues ." | clears senescent cellular waste |
| Bioquercetin phytosome | "Most important comprehensive senolytic polyphenol" | | |
| Other, RV, Fisiten, Luteolin, Rutin, pterostilbene | | | |
| CONSUME WITH (optional) | | | |
| DHA / EPA blend | "retinal essential fatty acids that reduce AMD risk and advanced AMD" | Supports photoreceptor health | The visual pathway essential fatty acid |

FORMULATION AND METHOD FOR SUPPORTING RETINAL HEALTH THEREBY REDUCING THE RISK OF AGE-RELATED MACULAR DEGENERATION (AMD)

CROSS-REFERENCE TO RELATED APPLICATIONS

This application claims the benefit of U.S. provisional application No. 62/817,949, filed 13 Mar. 2019, which is hereby incorporated by reference as though fully set forth herein.

BACKGROUND a. Field

The instant disclosure relates to comprehensively supporting retinal health, thereby leading to the prevention and treatment of Age-Related Macular Degeneration (AMD). In particular, the instant disclosure relates to a formulation including nutrient, vitamin, and mineral supplement components.

b. Background Art

Age-related macular degeneration (AMD) is the leading cause of vision loss in aging western societies, affecting between 2 and 20 million Americans, depending upon its stage and definition. AMD affects "cultural competence"—the ability to read newspaper-size print and safely drive an automobile. It eventually results in 50% of all blind rehabilitation admissions in the United States. The prevalence of AMD is projected to skyrocket, primarily due to aging but also due to environmental challenges and the continued degradation of the food supply, worsened by uninformed consumers, in all industrialized populations. The estimated global cost of visual impairment due to AMD is $343 billion, including $255 billion in direct health care costs. Furthermore, as much as $98 billion in direct costs is currently being spent to manage this disease in the US, Canada, and Cuba (WHO sub region AMR-A). (Flaxman S R, Bourne R R A, Resnikoff S, et al. (2017), Global causes of blindness and distance vision impairment 1990-2020: a systematic review and meta-analysis, *Lancet Glob Health,* 5 (12): e1221-e1234.) Clearly, AMD imposes immense direct and indirect societal costs, straining health care systems worldwide.

The seminal body of AMD-related data emanates from the Age-Related Eye Disease Studies (AREDS) undertaken under the direction of the National Eye Institute, National Institute of Health. These studies were carefully conceptualized by scientific subject matter working groups. This research has resulted in peer-reviewed publication of the AREDS I trial in October 2001, with 40 subsequent scientific reports through November 2019, and the AREDS II trial published in May 2013, with 21 subsequent scientific reports as of December 2019. (Age-Related Eye Disease Study 2 Research Group (2013) Lutein+zeaxanthin and omega-3 fatty acids for age-related macular degeneration: the Age-Related Eye Disease Study 2 (AREDS2) randomized clinical trial. JAMA 309 (19):2005-15.)

The current recommended "Standard of Care" for worldwide optometrists and ophthalmologists is the improved AREDS II formulation (May 2013). This approach involves supplementation of high-risk AMD patients with a daily nutritional supplement formulation with the following high grade clinically validated composition (500 mg ascorbic acid, 400 IU D alpha tocopherol, 80 mg zinc oxide, 2 mg copper oxide and 10 mg lutein/2 mg zeaxanthin xanthophyll carotenoids).

There has been a hierarchy of high quality, prospective human clinical randomized control trial (RCT) "gold standard" data forming the basis of the current "Standard of Care" by the US National Institute of Health/National Eye Institute. Yet, AMD is a multifactorial disease with an enormous and impressive body of secondary scientific peer-reviewed literature encompassing the fields of cellular microbiology, cellular physiology, in-vitro cell culture, animal models, epidemiology, epi-genetics, genetics, preventative medicine, environmental medicine, and visual science. To wit, all AMD patients are encouraged to consume more fruits and vegetables. While embracing carotenoids and vitamins C and E found in plant food, AREDS science has largely ignored senolytic "polyphenols," the largest area of recent inquiry among the more than 300,000 papers published in anti-oxidant research since the 1950s.

BRIEF SUMMARY

A formulation and method for preventing, reducing the risk of, and/or slowing the progression of Age-Related Macular Degeneration (AMD) are disclosed. The formulation includes optimal daily dosages of vitamin C, vitamin E, zinc, copper, lutein, and zeaxanthin.

In an embodiment, a composition comprises, on a daily dosage basis, each of the following: approximately 250-1,000 mg of vitamin C; approximately 30-100 IU of vitamin E; approximately 25-30 mg of zinc; approximately 500 mcg of copper; approximately 9-12 mg of lutein; and approximately 3-4 mg of zeaxanthin.

In another embodiment, a method of manufacturing a composition comprises blending approximately 250-1,000 mg of vitamin C, approximately 30-100 IU of vitamin E, approximately 25-30 mg of zinc, approximately 500 mcg of stable copper, approximately 9-12 mg of lutein, and approximately 3-4 mg of zeaxanthin into a suitable dosage form.

In another embodiment, a method for preventing or slowing progression of visual loss due to age-related macular degeneration comprises administering a daily dosage of approximately 250-1,000 mg of vitamin C, approximately 30-100 IU of vitamin E, approximately 25-30 mg of zinc, approximately 500 mcg of copper, approximately 9-12 mg of lutein, and approximately 3-4 mg of zeaxanthin to a subject in need thereof.

BRIEF DESCRIPTION OF THE DRAWINGS

FIG. 1 is a table describing the components of the enhanced AREDS II formulation.

FIG. 2 is a table describing the biochemical mechanisms of action of the enhanced AREDS II formulation.

FIG. 3 is a table describing the benefits of the components of the enhanced AREDS II formulation in general terms.

DETAILED DESCRIPTION OF EMBODIMENTS

The present disclosure enhances the current "Standard of Care" (e.g., the existing commercial 750 mg AREDS II gel capsules or the "AREDS II formulation" or "AREDS II") and is based on the discovery and development of an enhanced AREDS II formulation, which, when combined with widely available and inexpensive low dose nutrients, can more effectively slow the progression of AMD. The disclosure presents broad additional ocular and systemic health benefits, based upon contemporary medical science.

The presently disclosed enhanced AREDS II formulation maintains the six legacy nutritional components valued and validated in the National Institute of Health, National Eye Institute AREDS II trial, while judiciously modifying the dose and nutrient forms to create more physical space in the capsule and enhance the effect of the individual components.

The present disclosure also includes a method of modifying and enhancing the AREDS II "Standard of Care" legacy formulation, reflective of the latest ophthalmological and other medical science disciplines. For example, the method can include strengthening retinal health and thereby reducing the side effects of new anti-vascular endothelial growth factor drugs, such as the recent reports of inflammation and vasculitis with current treatments. (See retinaspecialist.com; Garcia-Quintenilla L, Luaces-Rodriquez A, Gil-Martinez M, Mondelo-Garcia C, et al. (2019) Pharmacokinetics of Intravitreal Anti-VEGF Drugs in Age-Related Macular Degeneration. Pharmaceutics, 11(8): E365).

In an embodiment, the low dose components of the enhanced AREDS II formulation can be placed within the existing 750 mg NIH/NEI AREDS II gel capsules that are taken twice per day (BID) by mouth with food or flavored DHA dominant fish oil. The presently disclosed formulation can optionally be co-consumed with a DHA (docosahexaenoic acid) and/or EPA (eicosapentaenoic acid) supplement. The exact oral dose of DHA/EPA can be determined by a simple blood spot epigenetic biomarker called the red blood cell Omega 3-Index test, as known to those of skill in the art.

In another embodiment, other systemic 'whole health' enhancing components, such as pre-biotics, probiotics, symbiotics, digestive enzymes and magnesium, for example, can also be co-administered in addition to or instead of DHA and/or EPA. Magnesium can be too bulky to put in a gel cap, but it is necessary for over 200 biochemical enzymes (including ocular enzymes) to work. Magnesium is also needed to help vitamin B1 work, and it creates a balance with calcium. Most of these components may be included in an accompanying inositol flavored liquid drink or medical food, or a gel cap/capsule, for example.

In another embodiment, the components of the enhanced AREDS II formulation are inexpensive, widely available, and relatively easy to manufacture and sell to an aging global public.

In another embodiment, the components of the enhanced AREDS II formulation are "Generally Recognized As Safe" (GRAS) and do not conflict with the use of common additional pabulum consumer multivitamin/mineral formulations, such as Centrum® or One-A-Day®.

In another embodiment, the presently disclosed formulation and method address the major risk factor for AMD, which is 'aging' itself, with inclusion of senolytic nutrients.

In another embodiment, the presently disclosed formulation and method address the two major post-AREDS II scientific issues: "High Zinc" and "AMD Genetic Subgroup Differences," as well as a third AMD Genetic Subgroup population who under-methylate.

In another embodiment, the presently disclosed formulation includes all three cofactors needed for primary first line cellular antioxidant enzymatic defense (catalase, superoxide dismutase, as well as selenium and riboflavin to support glutathione peroxidase and glutathione reductase, respectively).

In another embodiment, the present disclosure provides a method of stabilizing, slowing, or reversing/treating geographic atrophy, which is a subtype of AMD affecting approximately $\frac{1}{3}^{rd}$ of those afflicted with the condition.

In another embodiment, the presently disclosed formulation and method result in stem cell regeneration within the retina, where energized and activated gene networks can lead to improved structure and/or function.

In another embodiment, the presently disclosed enhanced AREDS II formulation can be scaled to 1, 2 or 3 or more capsules per day based upon an individual's weight and/or % body fat. For example, one capsule per day can be administered to individuals weighing about 100+/−25 pounds and/or having about 25% body fat. In another example, 2 capsules per day can be administered to individuals weighing about 200+/−25 pounds and/or having about 30% body fat. In yet another example, 3 capsules per day can be administered to individuals weighing about 300+/−25 pounds and/or having greater than about 35% body fat.

Modification of AREDS I and AREDS II Six-Component Legacy Formulation to Enhance Efficiency FIG. 1 is a table describing the components of the enhanced AREDS II formulation, including modified forms and dosages of the six-individual legacy AREDS II nutrient vitamin and mineral supplement components (Vitamin C, Vitamin E, Zinc, Copper, Lutein, and Zeaxanthin), as well as enhancing nutrients. Modifications to the six legacy components are based, in part, upon post-AREDS II clinical studies. The modified form of each of the six legacy vitamins and minerals provides enhanced efficacy via mechanisms summarized and categorized in the table shown in FIG. 2. The enhanced efficacy of the modified forms also creates space in the gel cap for additional low-dose AREDS II-enhancing nutrients.

Referring to FIG. 1, the dosage of Vitamin C in the enhanced AREDS II formulation can be reduced by 50% (to about 250 mg per day), as compared to the AREDS II formulation, to create space for the inclusion of a blend of quercetin (senolytic) dominant polyphenols that provide antioxidant-reducing power equivalent to 500 mg vitamin C, while also providing multiple mechanistic advantages in addressing multiple underlying pathophysiologic processes of AMD, well beyond vital but simple antioxidant protection.

The large dose of synthetic vitamin E in the AREDS II formulation (400 IU dl-alpha tocopherol acetate) has also been reduced in the enhanced AREDS II formulation to create additional space within the capsule. The enhanced AREDS II formulation includes a lower dose (e.g., about 30 IU) of the more efficacious fat-soluble vitamin E succinate. In addition, astaxanthin and selenium have been incorporated as AREDS II-enhancing nutrients, providing equally effective cell membrane lipo-peroxide protection. In another embodiment, which may be more costly, the enhanced AREDS II formulation can include a mixture of the 8 isomers of vitamin E (4 tocopherols and 4 tocotrienols).

The 80 mg dose of zinc oxide in the AREDS II formulation has been modified to about 25-30 mg of zinc carnosine in the enhanced AREDS II formulation. This modification lessens activation of the alternative complement pathway in genetically susceptible AMD carriers, thus reducing the chance of a hyper-immune response in these carriers. (Rojas-Fernandez C H, Tyber K (2017) Benefits, potential harms, and optimal use of nutritional supplementation for preventing progression of age-related macular degeneration.

*Ann Pharmacol* 51:1-7.) This is an issue in those homozygous for the chromosome 1 Complement Factor H (CFH) gene placing such individuals at higher genetic risk. The choice of zinc as zinc carnosine is also effective against ubiquitous worldwide Helicobacter Pylori gastrointestinal infection, thus enhancing the bioavailability of all other components of the formulation and improving the effectiveness of the enhanced AREDS II formulation for all AMD patients. (Matsukura T, Tanaka H (2000) Applicability of zinc complex of L-carnosine for medical use. *Biochemistry (Mosc.)* 65 (7): 817-23.) As zinc remains important to AMD patients, additional biochemical zinc enhancement is described below.

The AREDS II 2 mg dose of copper oxide, a powerful oxidant and divalent metal redox reactive disruptor of retinal health, has been completely eliminated and replaced with a much smaller dose (e.g., about 250 mcg) and more stable form of copper, copper sulfate chelate, in the enhanced AREDS II formulation. This typical form of copper can oxidize the ingredients in a gel cap (or bind to resveratrol in a capsule).

In the enhanced AREDS II formulation, the lutein/zeaxanthin ratio has been aligned with the typical human physiological dietary plasma ratio found within the composition of the blood. This requires slightly reducing lutein dose and increasing dietary zeaxanthin dose of the AREDS II formulation to achieve a 3:1 lutein:zeaxanthin serum ratio, as shown in FIG. 1.

Enhanced Core Six-Way Protection Against AMD

The following is a description of six ways in which the enhanced AREDS II formulations can protect against AMD.

1. Address Aging Retinal Cells With a Quercetin-Dominant Mixture of Polyphenols, Vitamin D3 and Vitamin B3 (Niacinamide).

The accumulation of senescent cells can prevent tissue repair and regeneration, leading to loss of physiological function. Senescent cells exert a larger degenerative effect on neighboring cells by acquiring Senescence-Associated Secretory Phenotypes (SASP) that release inflammatory cytokines, growth factors, and proteases. Senolytics are a class of molecules that a) efficiently and effectively induce cell death; and/or b) target pro-survival networks including p53/p21, Bcl-2, P13K/Akt and serpin pathways. (Richer S, Ulankski II, L, Popenko N A, et al., "Age-related Macular Degeneration Beyond the Age-related Eye Disease Study II" in Yannuzzi, *Advances in Ophthalmology and Optometry* 1 (Elsevier Press, 2016), pp. 335-369.)

Two inexpensive nutrients—quercetin and vitamin D3—address all senolytic pathways and work even more effectively with a mixture containing the somewhat more expensive fisetin, trans-resveratrol and/or pterostilbene (a methylated stilbene similar to trans-resveratrol). (Kozlowski M R (2012) RPE cell senescence: a key contributor to age-related macular degeneration. *Med Hypotheses* 78 (4): 505-10; Li W, Qin L, Hu G, et al. (2019) Emerging senolytic agents derived from natural products. *Mech Ageing Dev* 181:1-6.) These nutrients are not present in the current AREDS II "Standard of Care" formulation. Polyphenols, including quercetin, are widely distributed components of the plant kingdom and have myriad additional properties beyond free-radical scavenging that benefit AMD patients, including metal chelation, epigenetic gene signaling modulation, and anti-inflammatory effects. (Bungau S, Abdelp-Daim M M, Tit D M, et al. (2019) Health Benefits of Polyphenols and Carotenoids in Age-Related Eye Diseases. *Oxid Med Cell Longev* vol. 2019, Article ID 9783429, 22 pages).

The enhanced AREDS II formulation includes inexpensive niacinamide (vitamin B3 or nicotinamide) to promote and stabilize a coenzyme called NAD+ (nicotinamide adenine dinucleotide), a vital coenzyme for energizing cells and promoting youthful cellular processes. In epigenetic science, sirtuins are seven proteins required for optimal health, longevity and response to stress and injury. (Carafa V, Rotili D, Cuomo F, et al. (2016) Sirtuin functions and modulation: from chemistry to the clinic. *Clin Epigenetics* 8:61.) Trans-resveratrol or pterostilbenes stimulate sirtuin 1 protein production, which ultimately depend on an energetic supply of NAD+. This combination reduces the risk of developing AMD, whose major risk factor is aging, a process that occurs not linearly but exponentially at advancing age. Specifically, NAD+ improves mitochondrial function and inhibits stem cell senescence. (Zhang H, et al. (2016) NAD(+) repletion improves mitochondrial and stem cell function and enhances life span in mice. *Science* 352 (6292):1436-43.)

Another embodiment of the enhanced AREDS II formulation can include nicotinamide riboside another NAD+ precursor, a patented supplement.

Another embodiment of the enhanced AREDS II formulation can also include the set of four nucleoside monophosphates: adenosine monophosphate (AMP); cytidine monophosphate (CMP); guanosine monophosphate (GMP); and uridine monophosphate (UMP).

2. Address Three Large Genetic AMD Subgroups

Despite improved clinical outcome, there have been numerous post-AREDS I and post-AREDS II criticisms concerning the choice of nutrients, the dose of nutrients (particularly zinc) and the efficacy of the newest AREDS II formulation in terms of individual genetic AMD sub-populations who may respond adversely. Specifically, two genes (Complement Factor H (CFH), Chromosome 1 and ARMS2/HTRA1 gene, Chromosome 10), among a field of at least 35 known AMD-associated genes, describe 80% of the genetic risk of developing AMD, especially if one is a homozygous carrier with an allele from both mother and father. In addition, recent epigenetic data was unknown during the AREDS II working group supplement formulation period (pre-2008), reflecting a decade of scientific advancement beyond the AREDS II "Standard of Care". (Desnettre T J (2018) Epigenetics in Age-related Macular Degeneration (AMD). J Fr Ophtalmol 41(9): e407-e415.) Additionally, testing for these two genes is now widely available to the public via the 23andme.com testing service. Millions of consumers have used this service. A third multi-gene pathway involves under-methylation in genetically susceptible AMD patients manifested by the buildup of the oxidant homocysteine. (Christen W G, Cook N R, Chiuve S E, et al. (2018) Prospective study of plasma homocysteine, its dietary determinants, and risk of age-related macular degeneration in men. Ophthalmic Epidemiol. 25(1):79-88.)

a. Homozygous (HZ) Chromosome 1 AMD CFH subgroup vulnerability. The enhanced AREDS II formulation benefits this particular subgroup in the following ways:

Enhanced AREDS II formulation lowers zinc.

Enhanced AREDS II formulation enhances zinc absorption via inclusion of the B6 vitamin cofactor.

Enhanced AREDS II formulation dramatically lowers copper and improves the copper/zinc ratio.

b. HZ Chromosome 10 AMD mitochondria subgroup vulnerability. The enhanced AREDS II formulation benefits this particular subgroup in the following ways:

Enhanced AREDS II formulation includes the marine carotenoid astaxanthin that enhances mitochondrial function.

Enhanced AREDS II formulation includes vitamin B3 (niacinamide)+polyphenols (e.g., trans-resveratrol or pterostilbene), and vitamin K2/MK7 (see FIG. 2).

c. Undermethylation and/or B12 deficiency/high homocysteine results in 40% increased risk of AMD. This genetic at-risk subgroup is not addressed with the AREDS II formulation, or with conventional mass market multivitamins that utilize folic acid. About $\frac{1}{3}^{rd}$ of the adult population in the U.S. does not properly metabolize folic acid. Folic acid or folate facilitates DNA repair, and helps lower homocysteine. (Christen W G, Cook N R, Chiuve S E, et al. (2018) Prospective study of plasma homocysteine, its dietary determinants, and risk of age-related macular degeneration in men. *Ophthalmic Epidemiol.* 25 (1):79-88.) The enhanced AREDS II formulation benefits this particular subgroup in the following ways:

Enhanced AREDS II formulation contains bioavailable B12 (as well as B6 and "Food Folate") to lower homocysteine via the MTHFR (methylene tetrahydrofolate reductase) gene, the rate limiting enzyme in the methyl cycle.

Enhanced AREDS II formulation diminishes risk resulting from the widespread and long-term chronic use of Proton Pump Inhibiting Pharmaceuticals (PPIs) such as Prevacid®, that lowers the bioavailability of B vitamins.

Enhanced AREDS II formulation adjusts B12 dose higher than found in most pabulum multivitamins containing an inadequate 6-25 mcg dose of B12.

3. Provide Enhanced Foveola Carotenoid Protection (for More Resilient Cellular Membranes)

The enhanced AREDS II formulation focuses upon protection of the most valuable retinal "real estate," the central foveola, where 80% of catastrophic loss of vision occurs in the more advanced stages of AMD. The enhanced AREDS II formulation protects the foveola with naturally occurring zeaxanthin and improves retinal cell membrane stability as well as retinal blood flow with astaxanthin. In an embodiment, the enhanced AREDS II formulation includes higher dosed dietary zeaxanthin, 3 R 3'R, an isomer with an established long-term safety profile in AREDS II. (Age-Related Eye Disease Study 2 Research Group (2013) Lutein+zeaxanthin and omega-3 fatty acids for age-related macular degeneration: the Age-Related Eye Disease Study 2 (AREDS2) randomized clinical trial. *JAMA* 309 (19):2005-15.) In an embodiment, the enhanced AREDS II formulation contains 25% higher (e.g., 15 mg total) carotenoids, which addresses the increasingly unhealthy, aging, and obese US population with an increasingly higher percent body fat. More carotenoid protection is required for larger humans, as carotenoids are bound in fat before equilibrating with ocular tissues. The enhanced AREDS II formulation can be available as two capsules per day with meals, but can be used once per day for smaller humans (e.g., approx. 100 pounds) or three times per day for larger humans (e.g., approx. 300 pounds).

The enhanced AREDS II formulation reflects the plasma ratio of Lutein/Zeaxanthin (3:1) rather than the retinal ratio (5:1) by incorporating 9 mg lutein to 3 mg zeaxanthin.

The enhanced AREDS II formulation adds the marine carotenoid astaxanthin at a minimal dose of about 3 mg. In an embodiment, astaxanthin produced by Astrareal® may be used.

4. Anti-Calcify Bruch'S Retinal Membrane & the Small Blood Vessels of the Choriocapillaris Retinal Vasculature With Vitamin D3 and Vitamin K2/MK7

Bruch's membrane is an elastin/collagen matrix filter (blood-retinal barrier). Age-related or iatrogenic calcification of Bruch's membrane blocks the delivery of nutrients to the overlying retina, as well as efficient removal of biocellular waste. Calcification and AMD occurs more often in females, and particularly females with breast cancer calcifications who are 8.4 times more likely to develop AMD. (Kavroulaki D, Gugleta K, Kochkorov A, et al. (2010) Influence of Gender and Menopausal Status on Peripheral and Choroidal Circulation. *Acta Ophthalmologica* 88 (8): 850-53.)

The enhanced AREDS II formulation addresses the greater prevalence of AMD in females, in part due to females' diminished estrogen with age, calcium lost from bones with age, and longer life expectancy.

The enhanced AREDS II formulation addresses medically documented iatrogenic calcium supplementation imposed upon both females and males by many health professionals, including doctors, unaware of the risks to the retina, macro- and micro-vasculature and supportive tissues.

The enhanced AREDS II formulation improves upon the AREDS II supplement by including at least about 1400 IU (international units) of inexpensive vitamin D3 and the inclusion of long-acting vitamin K2/MK7. These two nutrients are crucial calcium managers, not present in the AREDS II formulation.

5. Enhance Anti-Neovascular Properties of the AREDS II Supplement

The enhanced AREDS II formulation augments the anti-neovascular properties of the AREDS II supplement. This is of prime importance in preventing catastrophic loss of vision from bleeding and scarring within the retina (exudative AMD).

The enhanced AREDS II formulation increases the actions of plasma vitamin C, thereby reducing Hypoxia Inducible Factor (HIF) beyond vitamin C itself, via inclusion of polyphenols, that bind CU++ and FE++. HIF promotes neovascularization, and these two environmentally common divalent minerals (CU++ and FE++) each promote neovascularization. The enhanced AREDS II formulation is anti-neovascular by virtue of inclusion of low dose polyphenols such as resveratrol or the methylated stilbene (pterostilbene) along with vitamin B3 (niacinamide). Additionally, this iron-free formulation utilizes a low and stable form of copper. The enhanced AREDS II formulation is anti-neovascular by virtue of the design of the capsule to maintain a desirable zinc:copper ratio (low copper). Resveratrol also creates collateral circulation in the event of arterial blockages in the heart while simultaneously inhibiting angiogenesis in the retina. Resveratrol is bidirectional. (Richer, Ulanski, Popenko, et al, AMD Beyond AREDS II, in Yannuzzi, Advances in Ophthalmology and Optometry 1 (2016), p 335-369, Elsevier Press.)

The enhanced AREDS II formulation is also anti-neovascular by virtue of inclusion of vitamin D3, an important fighter of neovascularization in both cancer and AMD. (Jamali N, Wang S, Darjatmoko S R, et al. (2017) Vitamin D receptor expression is essential during retinal vascular development and attenuation of neovascularization by 1, 25(OH)2D3. *PLoS One* 12 (12):e0190131). The DHA fraction of fish oil is also anti-neovascular.

6. Address Concomitant Insulin-Resistance/Non-Alcoholic Fatty Liver Disease, Epidemic Within the United States and a Driver of All Chronic Degenerative Diseases of Aging Insulin resistance is considered the sin qua non element in prevention of insulin resistance, which is the precursor for diabetes, an age-related disease that accelerates cardiovascular disease, a prime risk factor for AMD. Obesity and nonalcoholic fatty liver disease (NAFLD) affect well over 100 million Americans and are independent risk factors for cardiovascular diseases and oculovascular diseases including AMD. (Younossi Z, Anstee Q M, Marietti M. et al. (2018) Global burden of NAFLD and NASH: trends, predictions, risk factors and prevention. *Nat Rev Gastroenterol Hepatol.* 15 (1):11-20.) The enhanced AREDS II formulation promotes healthy glucose metabolism beyond the AREDS II supplement by synergizing with conventional pabulum multivitamins.

The enhanced AREDS II formulation contains allithiamine that passes the ocular-brain barrier and increases the transport of oxygen to the tissues. Benfotiamine, another fat-soluble form of vitamin B1 (thiamine), also works against the US epidemic of thiamin deficiency. Thiamine loss in the US diet results from over-consumption of soda, sweetened beverages, coffee, alcohol and carbohydrates, combined with miniscule replenishment in widely used pabulum multivitamins. Vitamin B1 supports healthy blood sugar, metabolism, and protects intracellular components of cells against advanced glycation end products (AGEs) due to sugar laden diets and aging itself. Allithiamine and benfotiamine, inexpensive at low doses, protect cells against oxidative stress, and are thus synergistic with AREDS II components.

The enhanced AREDS II formulation provides a blend of quercetin+polyphenols as well as vitamins B3 and D3 that are active against insulin resistance and NAFLD.

The enhanced AREDS II formulation, in one embodiment, can include the major nutrient of glucose tolerance factor (GTF) complex that is synthesized from absorbed dietary chromium III from brewer's yeast. (Yin R V, Phung O J (2015) Effect of chromium supplementation on glycated hemoglobin and fasting plasma glucose in patients with diabetes mellitus. *Nutr J.* 14:14.) This controversial transition mineral is a critical and vital nutrient supporting healthy glucose metabolism. GTF acts as a physiological enhancer of insulin activity, binding to insulin and potentiating its action about three-fold. This mineral has well established uses in preventive medicine against numerous cardiovascular ailments by supporting normal cellular glucose metabolism, healthy endothelial function, and normal cellular energy production. Chromium deficiency is common in the elderly, the obese, and those consuming processed foods.

Formula Evaluation

The enhanced AREDS II formulation will be evaluated by "Gold Standard" Clinical RCT (Double Blind, Double Masked, Randomized Controlled Clinical Trial), as it is believed that this scientific methodological approach can best evaluate the progression of AMD. It is believed that the unique selection of nutrients can more effectively prevent AMD compared to the 'Standard of Care' AREDS II supplement, by comparison. This belief is buttressed by his own record of published book chapters, articles, research and clinical studies as well as the work of other scientists. The enhanced AREDS II formulation may have additional ocular and public health benefits—e.g., reduction in risk of cataracts and glaucoma, and improved visual function (improved Snellen visual acuity, improved contrast sensitivity, improved glare recovery, improved glare disability, improved foveal shape discrimination, improved night driving abilities using validated questionnaires).

Unique Enhancements of the Enhanced AREDS II Formulation Beyond the AREDS II Supplement (Standard of Care)

The present disclosure applies the science of epigenetics to the clinical treatment of AMD, as others (Bruce Lipton, PhD, Deepak Das, PhD, Russell Jaffe, MD, PhD) have guided the application of epigenetics to the health of cells. The fate of retinal cells is not determined by one's DNA. Rather the fate of retinal cellular membrane health is modulated by the environment surrounding cells. Simply put, retinal cells can be thought of as fish living in an aquarium. The chemical composition of the blood determines the success of the community of billions of retinal cells to flourish, just as the water quality and nutrients reflect either healthy or unhealthy fish living in an aquarium. The blood is the culture medium and the composition of the blood represents the environment.

The enhanced AREDS II formulation includes the major categories of nutrients that are required for an enhanced cellular environment that enables the retina and microvasculature to flourish and remain healthy, even in the face of inherited AMD gene mutations, aging, excessive blue light, negative changes to the global food supply, and the increasing clinical use of intravitreal injections by ophthalmologists to treat advanced retinal disease.

The mechanisms of enhancing cellular environment are based on interpretation of available science and gaps in basic science with respect to cell culture, microbiology, biochemistry, genetics and smaller clinical studies. Smaller clinical studies, animal studies, and basic science support the individual enhancers used in the enhanced AREDS II formulation, the specific form of the vitamin and mineral selected, as well as justification for the specific design dosage minimum and range designated (see table in FIG. 1).

The enhanced AREDS II formulation moves well beyond the reductionist paradigm of high dose zinc (Newsome et al, late 1990s), antioxidants (NEI AREDS I, early 2000s) and additional retinal macular pigment enhancing nutrients lutein/zeaxanthin replacing B carotene (NEI AREDS II, 2013). The presently disclosed enhanced AREDS II formulation and methods incorporate new data and insights concerning senolytic nutrients, zinc, vitamin D3, vitamin K2, selenium, genes, gene networking, and, modification of the expression of those genes by controlling excess calcium, copper, and iron.

The components of the enhanced AREDS II formulation and related method provide the following benefits: 1) Reduce antecedent retinal A2E lipofuscin (antioxidants+lutein, zeaxanthin+polyphenols); 2) Reduce drusen (zeaxanthin, polyphenols); 3) Provide cofactors for antioxidant enzymes, not provided in AREDS II (selenium) which activates GSH peroxidase; 4) Reduces inflammation beyond AREDS II (astaxanthin, vitamins B3 and D3, polyphenols, selenium) thru epigenetic mechanisms; 5) Enhances the function of RPE (retinal pigment epithelial) mitochondria and peroxisomes thru epigenetic mitotropic support (astaxanthin, polyphenols, vitamin B3) thus supporting AMD subgroup chromosome 10 patients; 6) Enhances retinal micro capillary chroriocapillaris circulation (astaxanthin, polyphenols, vitamin D3, vitamin K2/MK7, conventional AREDS II antioxidants). The table shown in FIG. 2 summarizes the Six-Way Core Protection as additional enhancements well beyond the AREDS II supplement—and current "Standard of Care" prescribed by optometrists and ophthalmologists worldwide.

Current multivitamins and eye vitamins may fail to produce a beneficial effect to maintain eye health. The presently disclosed enhanced AREDS II formulation, taken alone or with optimized DHA rich fish oil. overcomes this shortcoming. Comprehensively, the enhanced AREDS II formulation provides the following benefits:
1. Inhibits angiogenesis, and therefore halts the most acute challenge to retinal health.
2. Delivers anti homocysteine nutrients
3. Delivers more oxygen to eye tissues
4. Eradicates drusen
5. Provides essential nutrients for eye health/lutein/zeaxanthin/EPA-DHA, which are part of retinal composition.
6. Facilitates dilation of arteries via nitric oxide
7. Thins the blood, inhibits clumping of platelets
8. Strengthens capillaries The table in FIG. 3 provides a generalized description of the benefits of the components of the enhanced AREDS II formulation.

Further Description of Specific Nutrients Included in the Enhanced AREDS II Formulation a. Quercetin Dominant Inexpensive Synergistic Polyphenol Blend The disclosed enhanced AREDS II formulation is built upon the core feature of a quercetin dominant synergistic polyphenol blend. Quercetin is the dominant inexpensive novel and useful bioactive flavonoid found in onions, apples and other botanicals, that can prevent obesity and offset the effects of damaging NAFLD (non-alcoholic fatty acid liver disease) driving systemic inflammation in two-thirds of the US population that are considered overweight or obese. Obesity with attendant abdominal inflammatory cytokine production is the driving force for the major degenerative diseases of aging including cardiovascular disease and cancer. Abdominal obesity, insulin resistance, and resultant cardiovascular disease are prime AMD "umbrella" risk factors, beyond aging and smoking. Adipose (fat tissue) accumulation with age is a powerful accelerator of cardiovascular diseases including AMD.

Quercetin's multitargeted molecular biochemical effects include: 1) up-regulation of AMPK (AMP-activated protein kinase), the anti-aging, metabolic regulatory signaling molecule; 2) rebalancing the gut microbiome and mitigating dysbiosis-related inflammatory and stress responses associated with cardiovascular degenerative diseases and diabetes; 3) downregulating expression of pro-inflammatory cytokine signaling molecules; and 4) reducing blood lipid levels, fat cell size and converting undesirable 'white fat cells' into more efficient 'brown fat cells'. (Xu D, Hu M J, Wang Y Q et al. (2019) Antioxidant Activities of Quercetin and Its Complexes for Medicinal Application. *Molecules* 24 (6): 1123.)

It is believed that environmental factors may be more influential than genetics in the control of retinal health. The presently disclosed enhanced AREDS II formulation provides a blend of small molecular weight polyphenol molecules that control microRNA gene networks implicated in AMD. These, in turn, are controlled by free (labile) retinal redox reactive divalent metals: iron and copper. Quercetin is a powerful binder of labile FE++, a divalent metal that controls gene networks. Other polyphenols such as resveratrol bind tightly to CU++. Epigenetic genes are modulated by these small molecular weight polyphenols not present in the AREDS II supplement, but nonetheless synergistic with its antioxidant benefit. (Richer S, Ulankski II, L, Popenko N A, et al., "Age-related Macular Degeneration Beyond the Age-related Eye Disease Study II" in Yannuzzi, Advances in Ophthalmology and Optometry 1 (Elsevier Press, 2016), pp. 335-369.)

Taken together, quercetin's inclusion in the disclosed formulation addresses multiple novel and useful mechanisms beyond the present Standard of Care for patients afflicted with AMD. In one embodiment, the disclosed formulation can incorporate quercetin phytosomes (i.e. *sophora* japonica from sunflowers), up to 50× more bioavailable than standard quercetin.

It has been shown that small polyphenol molecules in red wine concentrate activate stem cell retinal repair, serially improving visual function in patients now as old as 99 years. (Ivanova D, Richer S, Bhandari A. Improved Visual Acuity and Retinal Integrity with Resveratrol Based Supplementation in Patients with Macular Degeneration. *Ophthalmology and Clinical Research* ISSN: 2378-346X).

b. Selenium

The AREDS II formulation provides cofactors for at best 2 of the 3 first line cellular antioxidant enzymatic defense systems (Zinc (ZN)-Catalase and ZN/CU superoxide dismutase (SOD), but not the vital glutathione peroxidase enzyme (GPx), which requires selenium). One embodiment of the presently disclosed enhanced AREDS II formulation also includes the cofactor manganese for mitochondria Mn-SOD, although this mineral is not typically in short supply.

GPx couples with GSH reductase (a riboflavin or vitamin B2 dependent enzyme) to increase the major intracellular antioxidant in all living cells (glutathione or GSH), and especially abundant in the liver, brain and eyes. This is one basis of the Liver-Eye disease connection in 5000-year-old Chinese Medicine.

Selenium (SE), absent in the AREDS II supplement, is the cofactor for the GPx family promoting healthy cell division as well as thioredoxin reductase methionine sulfoxide reductase. In the disclosed enhanced AREDS II formulation, the selenium can use one, two or all three of the following forms for synergy: L-selenomethionine; L-selenocysteine (SelenoPure®) or sodium selenite. The form L-selenomethionine is required for ZN release and thus is involved in ZN homeostasis. ZN is universally deficient in the US population. ZN promotes the health of all five senses and supports the aging immune system as well as a healthy antioxidant response.

c. Vitamin B12

Vitamin B12 (methylcobalamin), absent in the AREDS II supplement, is the bioactive form of the vitamin that is readily used in the body and central nervous system. It is the main nutrient required to maintain the oxidant homocysteine in a normal range. Homocysteine elevation is an independent risk factor for developing AMD with age. B12 promotes normal nerve cell growth, and normal neural retinal cell growth specifically. It is thus useful and novel for treating geographic atrophy, an AMD subtype found in about one-third of those afflicted with the disease, for which the AREDS II supplement was not found to be beneficial in halting progression.

d. Vitamin D3

Vitamin D3 has a plethora of beneficial systemic and ocular effects, including restoring endothelium function and anti-neovascularization, beyond its historic role in calcium homeostasis. Vitamin D3 restores the essential balance between two key components required for healthy vascular endothelial function. It increases protective nitric oxide (NO) that dilates blood vessels while decreasing destabilizing and destructive peroxynitrite. Higher Vitamin D3 intake results in decreased retinal and choroidal circulatory arterial stiffness via the mechanisms of 1) decreased oxidative stress; 2) decreased glycation; and 3) decreased inflammation. Beyond its beneficial action on the ocular and systemic vasculature, Vitamin D3 is a hormone modulating over 1,000 genes, and it plays a role in modulating every stage of AMD.

Vitamin D3 is also a senolytic nutrient largely insufficient or deficient in older Americans. Vitamin D3 is particularly vital for housebound elderly living in northern latitudes of the world devoid of sunlight, or for those individuals who cannot afford to eat fish, or have been discouraged by their health care provider(s) to consume fish. Vitamin D3 is largely absent from all but a few ocular supplements, and it is insufficiently dosed in traditional widely available and widely consumed pabulum multivitamin/multimineral supplements (i.e. Centrum®, One-A-Day®).

The inclusion of vitamin D3 in the disclosed formulation boosts the dose available to counter AMD. Some 40-70% of the US public is insufficient or deficient, especially people of color, people living in northern US latitudes and citizens taking long-term acid blocking OTC or prescribed gastrointestinal Rx medications. The dose of 2,000 IU D3 (minimum 1400 IU D3 in the enhanced AREDS II formulation+600 IU D3 in a standard pabulum multivitamin) keeps 70% of the American public at risk for AMD replete, while providing beneficial senolytic protection. The disclosed formulation can scale to 3 capsules to provide additional vitamin D3 to obese patients.

e. Vitamin K2/MK7

Vitamin K2/MK7 is a calcium manager and present at a low dose in the disclosed formulation. The mal-distribution of systemic calcium plays a role in disease, and K2 MK7 is a long acting 'calcium manager' keeping labile calcium in bone, and out of Bruch's membrane. As well, excess misdirected labile calcium has a role in diminishing retinal blood flow in the small capillaries of the retina and choroid. This fat-soluble vitamin, is also an electron carrier and has anti-oxidant and mitochondrial enhancing properties. Vitamin K2 MK7 is normally produced by gut bacteria and is also present in aged cheese. The American public suffers from dysbiosis, and both their everyday vitamins and ocular vitamins do not typically contain vitamin K2 MK7.

f. Benfotiamine (S-benzoylthiamine O-monophosphate)

Benfotiamine is a novel fat-soluble Vitamin B1 derivative first used in Japan at a higher dose against alcoholic hepatic disease. Benfotiamine is more bioavailable than thiamine salts. It is inexpensive at low doses, and mitigates ubiquitous US thiamin deficiency through an increase in transketolose activity. It diminishes the adverse effects of dysglycemic mechanisms affecting all organs, including protection against developing diabetic retinopathy, nephropathy, neuropathy, and all ocular-vascular diseases, including AMD.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of manufacturing a composition comprising blending approximately 250-2,000 mg of vitamin C, approximately 30-100 IU of vitamin E, approximately 25-30 mg of zinc, approximately 250-500 mcg of stable copper, approximately 9-12 mg of lutein, approximately 3-4 mg of zeaxanthin, approximately 3-12 mg of astaxanthin, approximately 50-100 mcg of chromium, approximately 50 mcg to 100 mcg of selenium, approximately 5 to 10 mg of vitamin B1 (allithiamine and/or benfotiamine), approximately 50-250 mg of vitamin B3 (niacinamide), approximately 25-50 mg of vitamin B6 (pyridoxine), approximately 100-200 mcg of vitamin B9 (natural folate), approximately 150-300 mcg of vitamin B12 (methylcobalamin), approximately 50-200 mcg of vitamin D3, approximately 25-120 mcg of vitamin K2, approximately 250-1,000 mg of a polyphenol blend, and approximately 10-30 mg of bioquercetin phytosome into a suitable dosage form.

2. The method of claim 1, wherein the vitamin C comprises ascorbic acid; wherein the vitamin E comprises alpha-tocopherol succinate; wherein the zinc comprises at least one of zinc carnosine, zinc monomethionine, zinc citrate, and zinc acetate; wherein the copper comprises copper sulfate chelate; wherein the lutein comprises non-esterified lutein; and wherein the zeaxanthin comprises natural (3R-3'a) zeaxanthin.

3. The method of claim 1, further comprising approximately 30-100 mg of trans-resveratrol or pterostilbene into the suitable dosage form.

4. A method for preventing or slowing progression of visual loss due to age-related macular degeneration, the method comprising administering a daily dosage of approximately 250-2,000 mg of vitamin C, approximately 30-100 IU of vitamin E, approximately 25-30 mg of zinc, approximately 250-500 mcg of copper, approximately 9-12 mg of lutein, approximately 3-4 mg of zeaxanthin, approximately 3-12 mg of astaxanthin, approximately 50-100 mcg of chromium, approximately 50 mcg to 100 mcg of selenium, approximately 5 to 10 mg of vitamin B1 (allithiamine and/or benfotiamine), approximately 50-250 mg of vitamin B3 (niacinamide), approximately 25-50 mg of vitamin B6 (pyridoxine), approximately 100-200 mcg of vitamin B9 (natural folate), approximately 150-300 mcg of vitamin B12 (methylcobalamin), approximately 50-200 mcg of vitamin D3, approximately 25-120 mcg of vitamin K2/MK7, approximately 250-1,000 mg of a polyphenol blend, including approximately 10-30 mg of bioquercetin phytosome to a subject in need thereof.

5. The method of claim 4, further comprising administering a daily dosage of approximately 30-100 mg of trans-resveratrol or pterostilbene to the subject in need thereof.

6. The method of claim 4, further comprising administering a daily dosage of at least one of a DHA (docosahexaenoic acid) supplement and, optionally, a EPA (eicosapentaenoic acid) supplement.

7. The method of claim 4, wherein the daily dosage is based on the subject's weight or percent body fat.

* * * * *